United States Patent
Kollipara et al.

(10) Patent No.: US 10,143,754 B2
(45) Date of Patent: Dec. 4, 2018

(54) METHOD FOR PERORAL DELIVERY OF INSULIN AND ITS ANALOGUES FOR THERAPEUTIC USAGE

(75) Inventors: Koteswara Rao Kollipara, Hyderabad (IN); Gregory John Russell Jones, Middle Cove (AU)

(73) Assignee: TRANSGENE BIOTEK LIMITED, Andhra Pradesh (IN)

( * ) Notice: Subject to any disclaimer, the term of this patent is extended or adjusted under 35 U.S.C. 154(b) by 0 days.

(21) Appl. No.: 14/237,350

(22) PCT Filed: Aug. 7, 2012

(86) PCT No.: PCT/IB2012/054024
§ 371 (c)(1),
(2), (4) Date: Sep. 19, 2014

(87) PCT Pub. No.: WO2013/021346
PCT Pub. Date: Feb. 14, 2013

(65) Prior Publication Data
US 2015/0051142 A1    Feb. 19, 2015

(30) Foreign Application Priority Data
Aug. 7, 2011 (IN) .......................... 1228/CHE/2011

(51) Int. Cl.
| A61K 38/28 | (2006.01) |
| A61K 47/36 | (2006.01) |
| A61K 9/00 | (2006.01) |
| A61K 47/12 | (2006.01) |
| A61K 47/34 | (2017.01) |
| A61K 9/19 | (2006.01) |

(52) U.S. Cl.
CPC ............ *A61K 47/36* (2013.01); *A61K 9/0053* (2013.01); *A61K 9/19* (2013.01); *A61K 38/28* (2013.01); *A61K 47/12* (2013.01); *A61K 47/34* (2013.01)

(58) Field of Classification Search
CPC ..................................................... A61K 38/28
See application file for complete search history.

(56) References Cited

U.S. PATENT DOCUMENTS

| 6,159,502 A * | 12/2000 | Russell-Jones | A61K 9/167 424/489 |
| 6,869,938 B1 * | 3/2005 | Schwartz | A61K 47/10 514/42 |
| 2009/0098205 A1 * | 4/2009 | Sharma | A61K 9/5161 424/489 |
| 2012/0035103 A1 * | 2/2012 | Pillion | A61K 38/28 514/6.3 |

FOREIGN PATENT DOCUMENTS

| WO | WO 2001082937 | * 11/2001 |
| WO | WO 2006/113978 | * 11/2006 |

OTHER PUBLICATIONS

Baudys et al., Bioconjugate chem.9: 176-183, 1998.*
Silva et al., Eur. J. Pharm. Sci. 29: 148-159, 2006.*
Lin et al., Biomacromolecules 2007, 8:146-152.*
Wu et al., (Nanoscale Research Letters 2012, 7: 299 (electronic p. 1-8)).*
Wong T.W., J. Drug Targeting 18: 79-92, 2010.*
Solaro et al., 2010, 3: 1928-1980.*

* cited by examiner

*Primary Examiner* — Gyan Chandra
(74) *Attorney, Agent, or Firm* — Ladas & Parry LLP

(57) ABSTRACT

A method for treating type 1 and type 2 diabetes by administering an oral pharmaceutical formulation which comprises of insulin or its analogs amalgamated with suitable encapsulating agents and pharmaceutical excipients. The encapsulated pharmaceutical oral formulation protects insulin or its analogs from harsh milieu of the gastrointestinal tract and facilitates efficient delivery of insulin at targeted sites with sustained hypoglycemic activity.

6 Claims, 1 Drawing Sheet

METHOD FOR PERORAL DELIVERY OF INSULIN AND ITS ANALOGUES FOR THERAPEUTIC USAGE

TECHNICAL FIELD OF THE INVENTION

The present invention relates to a method of treating diabetes by oral administration of insulin or its analogues. More particularly, the present invention relates to a method for protecting insulin or/and its analogues from harsh milieu of the gastrointestinal tract and facilitate efficient delivery of the same to the targeted sites.

BACKGROUND OF THE INVENTION

Diabetes is considered as the world's fastest growing chronic disease. Patients with type 1 or type 2 diabetes have to inject insulin 3-4 times a day to maintain physiological glucose levels and it involves monitoring of blood glucose levels and administration of insulin injections every day for the rest of the diabetic patient's life.

Insulin therapy has evolved in the last century from using purified bovine or porcine insulin to biosynthetic human insulin to recombinant human insulin, and more recently to the use of recombinant insulin analogues, which represent the 3rd generation of human insulin (Hirsch 2005). Despite the great advances seen in the development of various types of insulin, the administration of insulin is still generally through subcutaneous route. Subcutaneous administration has lead to several treatment-associated sequelae. Insulin therapy or intensification of insulin therapy commonly results in weight gain in both Type 1 and Type 2 Diabetes (Kalra et al. 2010). This weight gain can be excessive and can adversely affect the patient's cardiovascular risk profile. This is possibly due to the 'unphysiological' pharmacokinetic and metabolic profile following subcutaneous administration. Thus, injected insulin can avoid first-pass metabolism, and therefore large quantities of insulin are available to stimulate adipocytes and increase glucose and lipid uptake into cells. High local concentrations of insulin may result in lipodystrophy, possibly due to areas of local down-regulation of insulin receptors in adjacent adipocytes (Regis et al. 2007). Further, due to the variation in the fat content under different sites of injection and variable release from the site of injection, it is often impossible to achieve strict glycemic control which leads to high variability in blood glucose levels between and within individuals.

Additionally, many patients are needle-phobic, and there is a high rate of non-compliance in diabetic patients, which leads to improper treatment and the development of undesirable sequelae that could have been prevented with correct treatment.

Recently, the potential for oral delivery of insulin has been explored by several workers (Madhav 2011). However, the use of oral delivery mechanisms for insulin is prevented by two main barriers. Firstly, the harsh acidic and proteolytic environment in the stomach and the intestine leading to rapid degradation of proteins such as insulin when administered orally; and secondly, there is a requirement to have a transport mechanism for insulin to be taken up and across the intestinal epithelial cells, with subsequent release into the circulation in pharmaceutically optimal concentrations (Madhav 2011).

The presence of insulin receptors in the upper part of the intestine has been reported (Buts et al, 1990, 1994, 1997a, 1997b; Fernández-Moreno et al, 1986, 1987, 1988; Forgue-Lafitte, 1980; Georgiev et al, 2003; Stilmant et al, 2001) and has the potential to be exploited for the gastrointestinal uptake of insulin. However, for it to be biologically active, Insulin has to be in its monomeric form. The purified insulin protein exists as a monomer at low pH, but self-associates to form a hexamer at basic pH. At pH in the range of 4.5 to 6.5, the insulin aggregates to form a precipitate. In order to utilize the naturally occurring receptors, there is a need for technology that can protect insulin from proteolytic degradation and maintain the conditions for insulin to be presented to its receptors in a monomeric form.

In the view of aforementioned limitations, there is a need to achieve efficient delivery of insulin through oral administration in its monomer form to avoid proteolysis in the gastrointestinal tract.

REFERENCES

Bendayan M, Ziv E, Gingras D, Ben-Sasson R, Bar-On H and Kidron M (1994) Biochemical and morphocytochemical evidence for the intestinal absorption of insulin in control and diabetic rats. Comparison between the effectiveness of duodenal and colon mucosa. Diabetologia 37:119-126.

Buts J P, De Keyser N, Kolanowski J, and Van Hoof F (1990) Hormonal regulation of the rat small intestine: responsiveness of villus and crypt cells to insulin during the suckling period and unresponsiveness after weaning Pediatr Res 27: 161-164.

Buts J P, De Keyser N, Marandi S, Maerrnoudt A S, Sokal E M, Rahier J, and Hermans D (1997a) Expression of insulin receptors and of 60-kDa receptor substrate in rat mature and immature enterocytes. Am J Physiol Gastrointest Liver Physiol 273: G217-G226.

Buts J P, De Keyser N, Romain N, Dandrifosse G, Sokal E M, and Nsengiyumva T. (1994) Response of rat immature enterocytes to insulin: regulation by receptor binding and endoluminal polyamine uptake. Gastroenterology 106: 58-68.

Buts J P, De Keyser N, Sokal E M, and Marandi S (1997b) Oral insulin is biologically active on rat immature enterocytes. J Pediatr Gastroenterol Nutr 25: 230-232.

Fernandez-Moreno M D, Arilla E and Prieto J C (1986) Insulin binding to rat intestinal epithelial cells following partial small-bowel resection. Biosci Rep. 6: 445-50.

Fernández-Moreno M D, Fernández-González M A, Diaz-Juárez J L, López-Luna M P and Prieto J C (1988) Interaction of insulin with small intestinal epithelial cells from developing rats. Biol Neonate. 54: 289-93.

Fernandez-Moreno M D, Serrano-Rios M and Prieto J C (1987) Identification of insulin receptors in epithelial cells from duodenum, jejunum, ileum, caecum, colon and rectum in the rat. Diabete Metab 13:135-139.

Forgue-Lafitte M E, Marescot M R, Chamblier M C and Rosselin G (1980) Evidence for the presence of insulin binding sites in isolated rat intestinal epithelial cells. Diabetologia. 19: 373-8.

Hirsch Irl B (2005) Insulin Analogues. N Engl J Med. 352:174-183.

Kalra S, Kalra B, Agrawal N (2010) Oral Insulin. Diabet Met Synd. 2: 66

King, G. L. and Johnson, S. (1985) Science 227: 1583-1586

Mutalik Madhav (2011) Long awaited dream of oral insulin: Where did we reach? Asian Journal of Pharmaceutical and Clinical Research. 4: 16-21.

R'egis P. Radermecker, G'erald E. Pi'erard and Andr'e J. Scheen (2007) Lipodystrophy Reactions to Insulin Effects of Continuous Insulin Infusion and New Insulin Analogs. Am J Clin Dermatol. 8: 21-28.

Stilmant, Mark H. Rider and Jean-Paul Buts (2001) Insulin signal transduction in rat small intestine: role of MAP kinases in expression of mucosal hydrolases. Am J Physiol Gastrointest Liver Physiol 280: G229-G240.

Wang Hong, Zhenqi Liu, Guolian Li and Eugene J. Barrett (2006) The vascular endothelial cell mediates insulin transport into skeletal muscle Am J Physiol Endocrinol Metab 291: E323-E332.

BRIEF SUMMARY OF THE INVENTION

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Exemplary objective of the subject matter is to deliver insulin or its analogues in the form of oral formulation for treating diabetic patients.

Another exemplary objective of the present invention is to maintain insulin in its monomeric form and deliver insulin or its analogues in biologically active state at the target sites.

Another exemplary aspect of the present invention is to provide insulin or its analogues with a suitable encapsulation agent to avoid proteolysis in the harsh environment of the gastrointestinal tract.

DETAILED DESCRIPTION OF THE INVENTION

Figure 1:
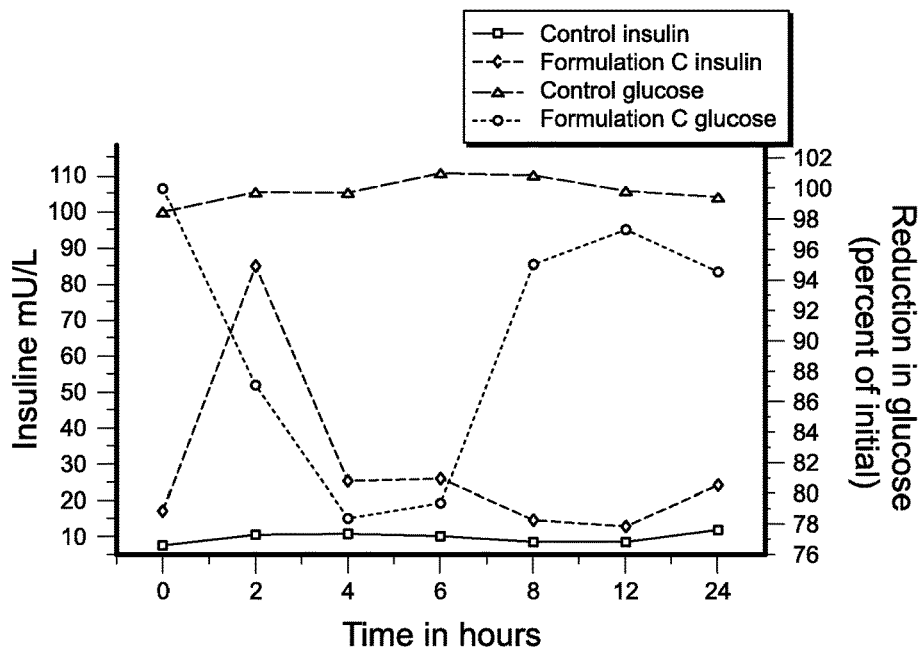
FIG. 1 illustrates a rapid reduction of blood glucose levels on IV administration of Insulin Lispro.

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

Exemplary embodiments of the present subject matter are directed towards an oral pharmaceutical formulation comprising proteins such as insulin and its analogues. The oral pharmaceutical formulation is amalgamated with suitable encapsulating agents to maintain insulin in its monomeric form providing protection from proteolysis in the harsh environment of the gastrointestinal tract.

According to the non limiting exemplary embodiments of the present subject matter, the oral delivery of the insulin into the diabetic patients results in appropriate pharmacological activity. The pharmacological activity may include but is not limited to modification of blood glucose levels in a diabetic host, promotion of muscle growth, initiating a decrease in body fat, an increase in fat-free muscle, improving lung function, strengthening connective tissue, improving brain activity and function, and increasing the rate of wound repair following surgery or trauma. The disclosed exemplary embodiments provide a method for treating both type 1 and type 2 diabetes through oral delivery of insulin or their analogues.

According to exemplary embodiments of the present subject matter, the suitable encapsulating agents include but are not limited to carboxymethyl cellulose, carboxymethyl dextran, chondroitin sulfate, chitosan, alginate, polyglutamic acid, polyaspartic acid, mixtures of calcium phosphate-PEG casein, cross-linked dextran, chitosan glucomannan as poly glutamic acid, poly aspartic acid and polylysine, poly (N-acylhydroxypropine esters; poly sebacic acid, poly fumaric acid, polylactic acid, poly glycolic acid, poly lactic-co-glycolic acid, carboxymethyl cellulose, gum arabic, alginate, polyphosphate, polylysine, heparin, gelatin, copolymers of sebacic acid and fumaric acid, copolymers of biscarboxyphenoxy propane and sebacic acid, poly(carboxyphoxyacetic acid), poly(carboxyphoxyvaleric acid), poly-e-caprolactone and related polyesters (poly-e-caprolactone-co-d-valerolactone; poly-e-caprolactoneco-DL-lactic acid), hyaluronic acid, chitin, chitosan, dextran, carboxydextran, collagen, albumin, fibrinogen and other naturally occurring polymers. The carriers can be mixed as powders, mixed as solutions, or formulated to make nanoparticle preparations. The surfactants can be mixed at varying w:w (weight:weight) ratios of 5:1 to 40:1 surfactant to insulin, or analogues thereof. The list of suitable carriers and surfactants disclosed herein may further include other carriers and surfactants generally used in the art that facilitate processing of the active compounds into preparations that may be used pharmaceutically. Further, the formulation may comprise of pharmaceutical excipients, solubilizers, diluents and preservatives well known in the art.

The purified insulin protein exists as a monomer at low pH, but self-associates to form a hexamer at basic pH. At pH in the range of 4.5 to 6.5, the insulin aggregates to form a precipitate. In order for insulin to exert its biological function in glucose reduction and for it to bind to the insulin receptor on the appropriate cell (liver, fat or muscle cell), it must be present in a monomeric form.

Unfortunately the pH of the gastrointestinal tract, particularly in the duodenum, is such that normal human insulin exists at best as a hexamer, and at worst as an aggregate. This, however, is not the case for other forms of insulin, such as Insulin Lispro and Insulin Aspart, and Insulin Glargine, which have been specifically designed either not to form hexameric aggregates or to be soluble at this lower pH. These molecules are currently administered by subcutaneous injection to stimulate rapid glucose reduction (rapid acting, Insulin Lispro or Insulin Aspart or Apidra®), or prolonged delayed release (Insulin Glargine). Disclosed embodiments are formulations of these analogues with suitable encapsulating agents which enable maximal uptake of insulin from the intestine due to the presence of monomeric form of insulin. It creates an optimal environment for monomeric form of insulin to be taken up by its own receptors present on the intestinal epithelial cells.

In another embodiment, the insulin present in the formulation upon binding to the insulin receptor of a cell is transported across cells and released on the opposite side of the cell.

This process of transcytosis has been found to occur on the vascular endothelium of muscle, which has been shown to transport insulin from the circulation into the interstitial space around the muscle cells (Wang et al, 2006). The insulin receptor has also been shown to be responsible for transcytosis of insulin across retinal endothelial cells (Bendayan and Rasio, 1996; King and Johnson, 1985), and is thought to be a general property of vascular endothelium (King and Johnson, 1985). This insulin receptor has been found to be expressed on the luminal surface of both neonatal and adult small intestine, and has a putative role in gut maturation in the neonate.

The embodiments disclosed herein are pharmaceutical formulations comprising insulin or its analogues. The insulin used in present invention may be obtained by isolating it from natural sources, or by chemically synthesizing it using peptide synthesis, or by using the techniques of molecular biology to produces recombinant insulin in bacteria or eukaryotic cells. The insulin originally from other species of mammal, such as bovine and porcine insulin, may also be used. The insulin, or insulin analogues may be of any type that is already known for effective glucose control. In order to obtain effective glucose control a variety of insulin analogues have, earlier, been synthesized with different activities. The variety of insulin analogues that may be used in the disclosed embodiments are as follows:

Rapid-Acting Insulin: Rapid acting insulin analogues act very quickly and are therefore usually administered just before a meal to minimize post meal rise in blood sugar. Three insulin analogues have been synthesized that have a rapid onset of action following injection which have been produced by genetically engineered insulin:

Lispro insulin, in which the amino acids lysine and proline at positions 28 and 29 of the insulin B-chain have been switched.

Insulin Aspart, in which Asp has been substituted for Pro at position 28 of the insulin B-chain.

Insulin Glulisine, in which lysine has been substituted for asparagine at position 3 of the insulin B-chain, and glutamic acid has been substituted for lysine at position 29 of the insulin B-chain.

These rapid acting insulin analogues have a rapid onset of action, at about 15-30 minutes after injection. The peak activity is at around 30-90 minutes after injection, and an effective duration of action of 4 to 5 hours when injected subcutaneously. This rapid onset of action is because these analogues are designed to inhibit the formation of the hexameric structures, which usually form with normal human insulin and thereby makes more insulin monomers available to bind to the insulin receptors.

Intermediate-Acting Insulin: Intermediate-acting insulin analogues start acting within the first hour of administration. This preparation has been produced by incubating zinc-insulin (human) with protamine to form an intermediate acting analogue (Neutral Protamine Hagedorn insulin, (NPH), with onset of action around 2 to 4 hours after injection and peak at 10 hours.

Long acting insulin: Long acting insulin analogues have no peak activity as such. They allow for consistent delivery of activity through the day. It is a modification of insulin, wherein glycine has been substituted for alanine at position 21 of the insulin A-chain plus two extra amino acids, both arginines, have been added at the end of the insulin B-chain, thereby extending it from its usual length of 30 amino acids to 32 amino acids. The resultant analogue, Insulin Glargine is soluble at acid pH, and forms a micro precipitate in the subcutaneous tissue that is at neutral pH. The insulin monomer slowly dissociates from this micro precipitate over a period of 20 to 24 hours.

According to exemplary embodiments of the present subject matter, insulin is isolated from suitable natural sources which may include but not limited to bovine or porcine pancreas. Insulin can also be isolated from chemical synthesis which may include but not limited to humulin and insulin can also be further isolated from molecular biological sources such as lispro, aspart, glargine and the like.

Referring to FIG. 1 is a graph illustrating a rapid reduction of blood glucose levels on IV administration of Insulin Lispro. The hypoglycemic effect was short lived. Similarly, the plasma insulin levels increased in accordance with the reduction in serum glucose levels but reduced rapidly with the same rate as reduction in hypoglycemic activity.

Figure 2:
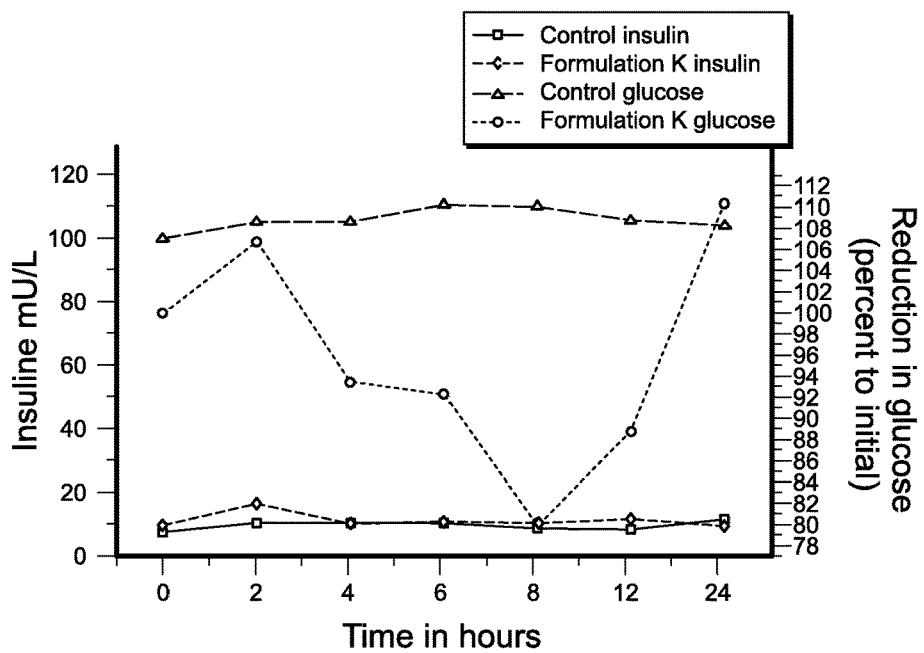
FIG. 2 illustrates sustained reduction in blood glucose levels upon oral administration of Insulin amalgamated in a suitable encapsulating agent.

Referring to FIG. 2 is a graph illustrating reduction in blood glucose levels upon oral administration of Insulin amalgamated in a suitable encapsulating agent. The drop in blood glucose levels was less rapid and sustained for a longer duration of time. An increase in the blood insulin levels was also observed indicating the movement of drug from intestinal lumen into the blood circulation.

According to the non limiting exemplary embodiments of the present subject matter, the orally administered insulin is formulated in such a manner that it is presented to the insulin receptor in an environment such as the optimal parameters being pH ranging between 1 to 10 and encapsulated with a suitable polymer.

According to the non limiting exemplary embodiments of the present subject matter, the orally administered insulin is transported from the intestinal lumen, across the epithelial cell and into the systemic circulation by the naturally occurring insulin-receptor that is found in both the neonatal and adult small intestine.

Exemplary embodiments of the present subject matter disclosed herein provide oral delivery of insulin or insulin analogues. The oral delivery of insulin is a convenient and much preferred route of administration. The oral administration of insulin through the various embodiments disclosed herein replicates the natural route of insulin secretion and absorption through the portal vein and targets the liver directly. The disclosed embodiments provide the delivery of insulin such that it is protected while in transit in the harsh adverse environment of the gastrointestinal tract.

The formulations disclosed in various embodiments herein can be delivered to a subject in various dosage forms well known in the art, which include a capsule, compressed tablet, pill, enteric coated capsule, enteric coated compressed tabled, enteric coated pill, solution, freeze-dried powder ready for reconstitution and suspension suitable for administration to the subject.

Also, those skilled in the art can appreciate from the foregoing description that the present invention can be implemented in the variety of forms. Therefore, while the embodiments of this invention have been described in connection with particular examples thereof, the true scope of the embodiments of the invention should not be so limited since other modifications will be apparent to the skilled practitioner upon a study of the drawings and following claims.

EXAMPLES

Example 1: General Method for the Preparation of Aliphatic Acid Structures that Contain Insulin Aliphatic acid (AA) is dissolved at 100 mg/ml in ethanol. The AA solution is then added to 0.25 M K2CO3 to give a final concentration of 5 mg/ml. The mixture is thoroughly mixed by vortexing and slowly added to an equal volume of 10 mM hydrochloric acid containing 5 mg/ml Insulin Lispro or its analogue. The solution was allowed to stir overnight, and was then stored at 4° C. before use.

Example 2: Use of Dodecanoic Acid for the Preparation of Aliphatic Acid Structures that Contain Insulin Dodecanoic acid (DDA) is dissolved at 100 mg/ml in ethanol. The DDA solution is then added to 0.25 M K2CO3 to give a final concentration of 5 mg/ml. The mixture is thoroughly mixed by vortexing and slowly added to an equal volume of 0.5 M citric acid containing 5 mg/ml Insulin Lispro or its analogue. The solution was allowed to stir overnight, and was then stored at 4° C. before use.

Example 3: Use of Tetradecanoic Acid for the Preparation of Aliphatic Acid Structures Containing Insulin Tetradecanoic acid (TDA) is dissolved at 100 mg/ml in ethanol. The TDA solution is then added to 0.25 M K2CO3 to give a final concentration of 5 mg/ml. The mixture is thoroughly mixed by vortexing and slowly added to an equal volume of 10 mM hydrochloric acid containing 5 mg/ml Insulin Lispro or its analogue. The solution was allowed to stir overnight, and was then stored at 4° C. before use.

Example 4: Use of Hexadecanoic Acid for the Preparation of Aliphatic Acid Structures Containing Insulin Hexadecanoic acid (HDA) is dissolved at 100 mg/ml in ethanol. The HDA solution is then added to 0.25 M K2CO3 to give a final concentration of 5 mg/ml. The mixture is thoroughly mixed by vortexing and slowly added to an equal volume of 10 mM hydrochloric acid containing 5 mg/ml Insulin Lispro or its analogue. The solution was allowed to stir overnight, and was then stored at 4° C. before use.

Example 5: Use of Octadecanoic Acid for the Preparation of Aliphatic Acid Structures Containing Insulin Octadecanoic acid (ODA) is dissolved at 100 mg/ml in ethanol. The ODA solution is then added to 0.25 M K2CO3 to give a final concentration of 5 mg/ml. The mixture is thoroughly mixed by vortexing and slowly added to an equal volume of 10 mM hydrochloric acid containing 5 mg/ml Insulin Lispro or its analogue. The solution was allowed to stir overnight, and was then stored at 4° C. before use.

Example 6: Use of Oleic Acid for the Preparation of Aliphatic Acid Structures Containing Insulin Oleic acid (OA) is dissolved at 100 mg/ml in ethanol. The OA solution is then added to 0.25 M K2CO3 to give a final concentration of 5 mg/ml. The mixture is thoroughly mixed by vortexing and slowly added to an equal volume of 10 mM hydrochloric acid containing 5 mg/ml Insulin Lispro or its analogue. The solution was allowed to stir overnight, and was then stored at 4° C. before use.

Example 7: Use of Palmitoleic Acid for the Preparation of Aliphatic Acid Structures Containing Insulin Palmitoleic acid (PA) is dissolved at 100 mg/ml in ethanol. The PA solution is then added to 0.25 M K2CO3 to give a final concentration of 5 mg/ml. The mixture is thoroughly mixed by vortexing and slowly added to an equal volume of 0.5 M citric acid containing 5 mg/ml Insulin Lispro or its analogue. The solution was allowed to stir overnight, and was then stored at 4° C. before use.

Example 8: Use of Ricinoleic Acid for the Preparation of Aliphatic Acid Structures Containing Insulin Ricinoleic acid (RA) is dissolved at 100 mg/ml in ethanol. The RA solution is then added to 0.25 M K2CO3 to give a final concentration of 5 mg/ml. The mixture is thoroughly mixed by vortexing and slowly added to an equal volume of 10 mM hydrochloric acid containing 5 mg/ml Insulin Lispro or its analogue. The solution was allowed to stir overnight, and was then stored at 4° C. before use.

Example 9: Use of Fusidic Acid for the Preparation of Aliphatic Acid Structures Containing Insulin Fusidic acid (FA) is dissolved at 100 mg/ml in ethanol. The FA solution is then added to 0.25 M K2CO3 to give a final concentration of 5 mg/ml. The mixture is thoroughly mixed by vortexing and slowly added to an equal volume of 10 mM hydrochloric acid containing 5 mg/ml Insulin Lispro or its analogue. The solution was allowed to stir overnight, and was then stored at 4° C. before use.

Example 10: General Method for the Preparation of Polyanionic Structures that Contain Insulin Polyanions (PA) are dissolved at 25 mg/ml in distilled water. The mixture is thoroughly mixed by vortexing and the pH titrated ranging between 1 to 8 with a suitable acid or base. An equal volume of 10 mM hydrochloric acid containing 5 mg/ml insulin Lispro is slowly added to the PA solution and stirred for a further hour. The solution was lyophilized and stored dry until used.

Example 11: Method for the Preparation of Polyanionic Structures with Carboxy-Methyl Dextran and Insulin Carboxymethyl dextran (CMD) was dissolved at 80 mg/ml in distilled water. The mixture was thoroughly mixed by vortexing and the pH titrated ranging between 1 to 8 with a suitable acid or base. A stock of Insulin Lispro prepared by dissolving 100 mg/ml in 0.1M HCl. Insulin stock and CMD mixed in the ratios ranging from 1:5 to 1:40 weight by weight.

Example 12: Method for the Preparation of Polyanionic Structures with Alginic and Insulin Alginic acid was dissolved at 5 mg/ml in distilled water. The mixture was thoroughly mixed by vortexing and the pH titrated ranging between 1 to 8 with a suitable acid or base. A one-fifth 1 volume of 10 mM hydrochloric acid containing 5 mg/ml Insulin Lispro is slowly added to the alginic acid solution and stirred for a further hour. The solution was lyophilized and stored dry until used.

Example 13: Method for the Preparation of Polyanionic Structures with Hyaluronic Acid and Insulin Hyaluronic acid was dissolved at 5 mg/ml in distilled water. The mixture was thoroughly mixed by vortexing and the pH titrated ranging between 1 to 8 with a suitable acid or base. A one-fifth 1 volume of 10 mM hydrochloric acid containing 5 mg/ml Insulin Lispro is slowly added to the hyaluronic acid solution and stirred for a further hour. The solution was lyophilized and stored dry until used

Example 14: Method for the Preparation of Polyanionic Structures with Polyglutamic Acid and Insulin Polyglutamic acid was dissolved at 255 mg/ml in distilled water. The mixture was thoroughly mixed by vortexing and the pH titrated ranging between 1 to 8 with a suitable acid or base. An equal volume of 10 mM hydrochloric acid containing 5 mg/ml Insulin Lispro is slowly added to the polyglutamic acid solution and stirred for a further hour. The solution was lyophilized and stored dry until used

Example 15: Method for the Preparation of Polyanionic Structures with Polyaspartic Acid and Insulin Polyaspartic acid was dissolved at 255 mg/ml in distilled water. The mixture was thoroughly mixed by vortexing and the pH titrated to ranging between 1 to 8 with a suitable acid or base. An equal volume of 10 mM hydrochloric acid containing 5 mg/ml Insulin Lispro is slowly added to the polyaspartic acid solution and stirred for a further hour. The solution was lyophilized and stored dry until used.

Example 16: Modification of Serum Glucose of Diabetic Rats Receiving Insulin Lispro Formulated within Aliphatic Acids According to the Invention Streptozotocin induced diabetic Wistar or Sprague Dawley rats were placed in a restraining apparatus and a blood sample was obtained from the tail vein or orbital sinus of the conscious rats. The rats then received by gavage feeding a 1 mg dose of Insulin Lispro formulated in encapsulating agents. At 2, 4, 6, 8, 12, 24 & 48 h following injection the rats were bled from the tail vein and plasma prepared from the collected blood. Plasma glucose was measured using an auto analyzer and insulin levels estimated by using an iso-insulin ELISA kit.

Example 17: Modification of Serum Glucose of Diabetic Rats Receiving Insulin Lispro Formulated within Carboxymethyl Dextran According to the Invention Streptozotocin induced diabetic Wistar or Sprague Dawley rats were placed in a restraining apparatus and a blood sample was obtained from the tail vein of the conscious rats. The rats then received by gavage feeding a 1 mg dose of Insulin Lispro formulated in carboxymethyl dextran. At 2, 4, 6, 8, 12, 24 & 48 h following injection the rats were bled from the tail vein or orbital sinus and plasma prepared from the collected blood. Plasma glucose was measured using an auto analyzer and insulin levels estimated by using an iso insulin ELISA kit.

The invention claimed is:

1. A method for treating diabetes comprising orally administering a pharmaceutical formulation to a subject, wherein the oral pharmaceutical formulation comprises insulin encapsulated with a suitable encapsulating agent and a pharmaceutical excipient, and wherein the encapsulating agent consists of carboxymethyl dextran, and wherein the formulation enables uptake of insulin by insulin receptors naturally occurring in an intestine of a patient and is not in the form of a nanoparticle preparation.

2. The method according to claim 1, wherein the pharmaceutical excipient is selected from the group consisting of surfactants, diluents, carriers, solubilizers and preservatives.

3. The method according to claim 1, wherein a weight ratio of the pharmaceutical excipient to insulin ranges from 5:1 to 40:1 to alter the a degree of encapsulation.

4. The method according to claim 1, wherein the administered insulin reaches target site at an optimal environment at appropriate optimal parameters.

5. The method according to claim 4, wherein the optimal parameters pH ranges from 1 to 10.

6. A method for treating a patient with either type 1 or type 2 diabetes comprising orally administering a pharmaceutical formulation to the patient, wherein the oral pharmaceutical formulation comprises insulin or its analogues encapsulated with a suitable encapsulating agent and a pharmaceutical excipient, wherein the encapsulating agent consists of carboxymethyl dextran, and wherein the formulation enables uptake of insulin by insulin receptors naturally occurring in an intestine of the patient and is not in the form of a nanoparticle preparation.

* * * * *